United States Patent [19]

Naito et al.

[11] 4,206,116
[45] Jun. 3, 1980

[54] NOVEL PENICILLINS

[75] Inventors: Takayuki Naito, Kawasaki; Jun Okumura, Yokohama; Hideaki Hoshi, Ichikawa, all of Japan

[73] Assignee: Bristol-Myers Company, New York, N.Y.

[21] Appl. No.: 967,338

[22] Filed: Dec. 7, 1978

Related U.S. Application Data

[63] Continuation-in-part of Ser. No. 951,900, Oct. 16, 1978, abandoned.

[51] Int. Cl.² .......................................... C07D 499/44
[52] U.S. Cl. ................................. 260/239.1; 424/250
[58] Field of Search ..................................... 260/239.1

[56] References Cited

U.S. PATENT DOCUMENTS

| 4,087,424 | 5/1978 | Saikawa et al. | 260/239.1 |
| 4,110,327 | 8/1978 | Saikawa et al. | 260/239.1 |

FOREIGN PATENT DOCUMENTS 1450764  9/1976  United Kingdom ................ 260/239.1

Primary Examiner—Norman Morgenstern
Assistant Examiner—Vera C. Clarke
Attorney, Agent, or Firm—H. W. Taylor, Jr.

[57] ABSTRACT

The penicillin of the formula

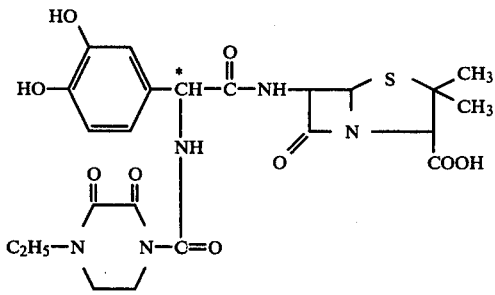

and its pharmaceutically acceptable salts and physiologically hydrolyzed esters possess antibacterial activity and are particularly valuable in treating Pseudomonas infections.

9 Claims, No Drawings

NOVEL PENICILLINS

CROSS REFERENCE TO RELATED APPLICATION

This application is a continuation-in-part of our prior, copending application Ser. No. 951,900 filed Oct. 16, 1978, now abandoned.

BACKGROUND OF THE INVENTION

1. Field of the Invention

The novel semi-synthetic penicillin of the present invention is useful as an antibacterial agent for the treatment of bacterial infections caused by Gram-positive and Gram-negative bacteria.

2. Description of the Prior Art

D-α-Amino-α-(3,4-dihydroxyphenyl-)acetamidopenicillanic acid is a known antibacterial agent described, for example, in U.K. Pat. No. 1,450,764.

Penicillins of the formula

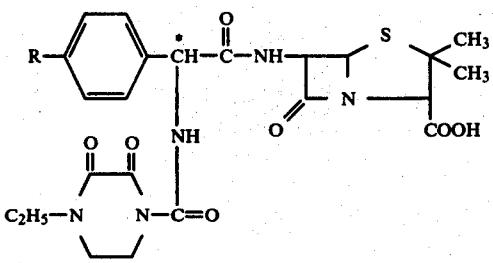

wherein R is hydrogen or hydroxy are described among others in U.S. Pat. No. 4,087,424 as, for example, in Examples 11, 13 and 22–24 and in column 45. See also the recently issued U.S. Pat. No. 4,112,090.

SUMMARY OF THE INVENTION

The present invention provides the acid of the formula

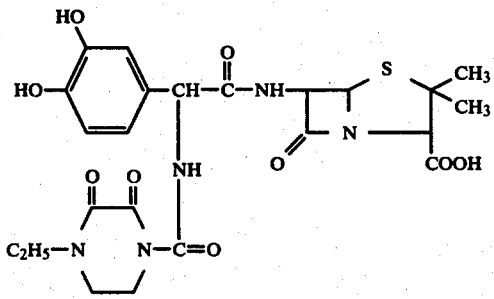

having the D-configuration in the 6-sidechain or a pharmaceuticaly acceptable salt thereof or an easily hydrolyzed ester thereof.

The pharmaceutically acceptable salts referred to above include nontoxic metallic salts such as sodium, potassium calcium and magnesium, the ammonium salt and substituted ammonium salts, e.g. salts of such nontoxic amines as trialkylamines (e.g. triethylamine), procaine, dibenzylamine, N-benzyl-β-phenethylamine, 1-ephenamine, N,N'-dibenzylethylenediamine, dehydroabietylamine, N,N'-bis(dehydroabietyl)ethylenediamine, N-(lower)alkyl-piperidine (e.g. N-ethylpiperidine) and other amines which have been used to form pharmaceutically acceptable salts of penicillins and cephalosporins. The most preferred salts are the alkali metal salts, i.e. the sodium and potassium salts.

As used herein the term "physiologically hydrolyzed esters" refers to those pharmaceutically acceptable esters (of penicillins or cephalosporins) known in the art to hydrolyze to the free acid form in vivo. Esters of this type are described, for example, in U.S. Pat. Nos. 3,859,274, 3,860,570, 3,860,579, 3,864,331, 3,873,521 and 3,919,196, in U.K. patent specifications Nos. 1,215,812, 1,267,936, 1,425,571, and 1,400,584, and German Published Applications 1,951,012 and 2,230,620. Examples of suitable physiologically hydrolyzed esters include acetoxymethyl, pivaloyloxymethyl, α-acetoxyethyl, α-acetoxybenzyl, α-pivaloyloxyethyl, phthalidyl(3-phthalidyl), indanyl(5-indanyl), methoxymethyl, benzoyloxymethyl, α-ethylbutyryloxymethyl, propionyloxymethyl, valeryloxymethyl and isobutyryloxymethyl. The preferred esters are the acetoxymethyl, pivaloyloxymethyl, methoxymethyl, phthalidyl and 5-indanyl esters, most preferably acetoxymethyl, methoxymethyl and pivaloyloxymethyl.

DETAILED DESCRIPTION OF THE INVENTION

The penicillin of the formula

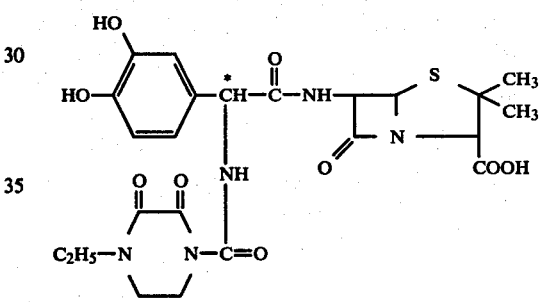

is prepared according to one procedure by reacting a compound of the formula

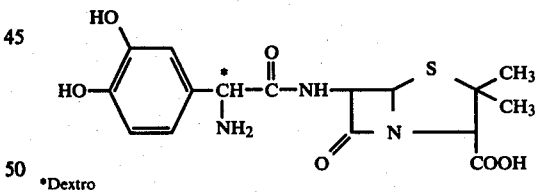

*Dextro or a salt or easily cleavable ester thereof with an acylating agent of the formula

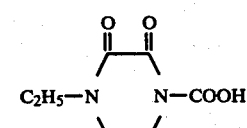

or with a reactive acylating derivative thereof and, if the reaction product contains an easily cleavable ether protecting group, optionally removing said protecting group by a method known per se and, if desired, converting by a method known per se (a) the product in the form of a free acid to a pharmaceutically acceptable salt or a physiologically hydrolyzed ester thereof, or (b) the product in the from of a salt to the free acid or a pharmaceutically acceptable salt or a physiologically hydrolyzed ester thereof. The above acylation reaction may be carried out by methods which are themselves known in the art, e.g. from the synthesis of peptides, penicillins and cephalosporins.

The starting material penicillins of formula II are known compounds. Preparation of the acylating acid starting material III is described below.

In the acylation of the α-amino group of penicillin II, the carboxylic acid of formula III may be used per se in which case it is preferred to use an enzyme or a condensing agent. Suitable condensing agents include N,N'-dimethylchloroformiminium chloride, an N,N'-carbonyldiimidazole or an N,N'-carbonylditriazole, a carbodiimide reagent (especially N,N'-dicyclohexylcarbodiimide, N,N'-diisopropylcarbodiimide or N-cyclohexyl-N'-(2-morpholinoethyl)carbodiimide, alkylylamine reagent, an isoxasolium salt reagent, ketenimine reagent, hexachlorocyclotriphosphatriazine or hexabromocyclotriphosphatriazine, diphenylphosphoryl azide (DPPA), diethylphosphophosphorylcyanide (DEPC), diphenylphosphite or N-ethoxycarbonyl-2-ethoxy-1,2-dihydroquinoline (EEDQ).

As an alternative to using the carboxylic acid III in the above process, there may also be employed reactive acylating derivatives of acid III, i.e. functional equivalents of the acid as acylating agents for a primary amino group. Examples of reactive acylating derivatives of the carboxylic acid include the acid halide (e.g. acid chloride or acid bromide), acid anhydrides, including mixed anhydrides (e.g. alkoxyformic anhydrides), acid azides, active esters (e.g. p-nitrophenyl) and active thioesters. Another reactive derivative of the acid is a corresponding azolide, i.e. an amide of the acid whose amide nitrogen is a member of a quasiaromatic five-membered ring containing at least two nitrogen atoms, i.e. imidazole, pyrazole, the triazoles, benzimidazole, benzotriazole and their substituted derivatives. The general method for preparation of azolides is described, for example, in U.S. Pat. No. 3,910,900.

Mention was made above of the use of enzymes to couple the free acid with compound II. Included in the scope of such processes are the use of an ester, e.g. the methyl ester, of that free acid with enzymes provides by various microorganisms, e.g. those described in J. Am. Chem. Soc., 94(11), 4035–4037 (1972), J. Antibiotics (Japan), 24(5), 321–232 (1971) and U.S. Pat. No. 3,682,777.

Acylation with the carboxylic acid III or reactive acylating derivative thereof may be carried out on the peniacillanic acid of formula II or a salt (e.g. an alkali metal or an amine salt) or easily cleavable ester thereof.

The term "easily cleavable ester" refers to a derivative of the penicillanic acid in which the 3-carboxyl group has been protected by any of the known ester protective groups capable of being removed following the acylation reaction by methods, e.g. chemical or enzymatic hydrolysis, treatment with chemical reducing agents under mild conditions, irradiation with ultraviolet light or catalytic hydrogenation, which do not result in any appreciable destruction of the remaining portion of the molecule. Examples of suitable "easily cleavable esters" include trialkylsilyl (e.g. trimethylsilyl) and other esters derived from silyl alcohol or stannyl alcohol which can be removed by solvolysis with a solvent containing hydroxyl groups, t-butoxycarbonyl, benzhydryl, benzyl, p-nitrobenzyl, p-methoxybenzyl, 2,2,2-trichloroethyl, phenacyl, acetonyl, p-bromophenacyl, (lower)alkyl such as methyl, ethyl or t-butyl and the physiologically hydrolyzed esters mentioned above. The general methods for the preparation of these esters and for their removal are described in the literature and are well-known to those skilled in the art.

The acylation process is conducted in a reaction-inert solvent system which can be aqueous or non-aqueous. Suitable reaction-inert solvents include, for example, water, acetone, tetrahydrofuran, dioxane, acetonitrile, dimethylformamide, dimethylsulfoxide, methylene chloride, chloroform, benzene, toluene, methyl isobutyl ketone and mixtures of the above-mentioned organic solvents with water. The choice of solvent, i.e. particularly whether an aqueous or non-aqueous solvent is used, is dependent on the particular starting materials employed. Thus, for example, if the penicillin starting material II is used in the form where the 3-carboxyl moiety is protected by an ester group cleaved by hydroxylic solvents, e.g. a silyl or stannyl ester, an aprotic organic solvent is most preferably employed. Also, when the penicillin of formula II is used in its salt form, water or an aqueous organic solvent system is preferably employed. The most advantageous solvent system for the particular reagents used can be determined by routine experimentation.

The duration and temperature of the acylation reaction are not critical. Temperatures in the range of from about −30° C. to about +50° C. are commonly used for reaction times ranging from less than one hour up to a day or more. Although the initial contacting of the reactants is preferably carried out at around 0° C. to reduce the incidence of by-products, it is frequently desirable after a few minutes of mixing to allow the reaction mixture to warm to room temperature until the reaction is complete.

The reactants of formulae II and III are normally employed in approximate equimolar quantities, although an excess of either can be used if desired.

When a carboxyl-protecting group is present in the product of the acylation reaction, it may be eliminated, if desired, in a per se conventional manner to give the desired 3-carboxylic acid penicillin or a salt thereof.

The acylation product is isolated in a conventional manner as the free acid or as a salt or as a physiologically hydrolyzed ester (if the appropriate ester group has been used in the acylation process). The free acid can be converted to a pharmaceutically acceptable salt thereof by treatment with an appropriate organic or inorganic base. The carboxylate salts may be converted to the free acids by treatment with an acid or suitable ion exchange resin. The product in the form of the free acid or salt thereof may also be converted by known methods to a corresponding physiologically hydrolyzed ester such as the pivaloyloxymethyl, acetoxymehtyl, phthalidyl, 5-indanyl or methoxymethyl esters.

An alternative process for preparing the penicillins of formula I comprises reacting 6-aminopenicillanic acid or a salt or easily cleavable ester thereof with an acylating agent of the formula

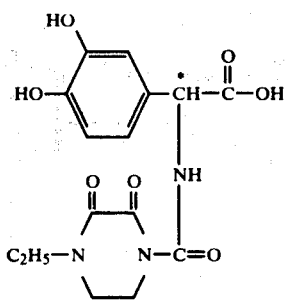

*Dextro having the D-configuration at the α-carbon atom or a reactive acylating derivative thereof and, if the reaction product contains an easily cleavable ester protecting group, optionally removing said protective group by a method known per se and, if desired, converting by methods known per se (a) the product in the form of a free acid to a pharmaceutically acceptable salt or a physiologically hydrolyzed ester thereof, or (b) the product in the form of a salt to the free acid or a pharmaceutically acceptable salt or a physiologically hydrolyzed ester thereof.

The terms "easily cleavable ester", "reactive acylating derivative", "pharmaceutically acceptable salt" and "physiologically hydrolyzed ester" used above in the description of the alternative process are as defined previously.

The acylation conditions, i.e. solvents, temperatures, molar ratios and isolation procedures, for this process are substantially the same as those described in connection with the first-mentioned process.

While, as indicated above, the penicillin derivatives of the present invention are useful antibacterial agents in themselves, they are particularly useful when used in combination with the aminoglycoside antibiotic, amikacin (or a pharmaceutically acceptable acid addition salt thereof), disclosed, for example, in U.S. Pat. No. 3,781,268. In another aspect, therefore, the present invention provides a pharmaceutical composition comprising (A) a penicillin derivative of formula I above, or a pharmaceutically acceptable salt or physiologically hydrolyzed ester thereof as defined above and (B) the aminoglycoside antibiotic, amikacin (1-[L-(−)-γ-amino-α-hydroxybutryl]kanamycin A), or a pharmaceutically acceptable acid addition salt thereof, optionally in admixture with a pharmaceutically acceptable carrier or diluent.

As used herein, the term "pharmaceutically acceptable acid addition salt" used in reference to amikacin refers to those pharmaceutically acceptable acid addition salts disclosed in U.S. Pat. No. 3,781,268 as being included within the scope of the invention claimed therein. Thus, suitable salts of amikacin include mono-, di-, tri- or tetra salts formed with such pharmaceutically acceptable acids as acetic, hydrochloric, sulfuric, maleic, phosphoric, nitric, hydrobromic, ascorbic, malic and citric acids. A most preferred amikacin salt is amikacin disulfate (amikacin sulfate).

Pharmaceutical compositions comprising both a penicillin of formula I (or a pharmaceutically acceptable salt or a physiologically hydrolyzed ester thereof) and amikacin (or a pharmaceutically acceptable acid addition salt thereof) possess many advantages over compositions comprising only one or the other of the two antibiotic components. Thus, a broadened antibacterial spectrum can be achieved since amikacin is antibacterially effective against organisms not affected by the penicillin, and vice versa. The potential nephrotoxicity and ototoxicity problems associated with the aminoglycoside antibiotic can be reduced by administration of a synergistic antibacterial combination product which permits a lower dosage of the aminoglycoside to achieve the same therapeutic effect. Reduced amikacin doses made possible by the synergistic combination product might also allow patients suffering from Pseudomonas infections to be treated with this highly effective antibiotic composition for a longer period of time than currently recommended for amikacin therapy (currently a 15 day limit is recommended).

The therapeutic penicillin-aminoglycoside compositions of the present invention may be administered to mammals, including man, by injection. The compositions may have optionally incorporated therewith standard pharmaceutically acceptable solid or liquid carriers or diluents. Other suitable dosage unit forms may be prepared according to known methods of the pharmaceutical industry.

The relative amount of the active ingredients in the combination according to the present invention may vary between wide ranges depending on the particular organism being treated and the choice of the physician as to whether to favor one or the other of the antibiotic components in treating a particular patient. A preferred weight ratio of the components found to provide synergistic bactericidal results against the four *Pseudomonas aeruginosa* strains mentioned above is between about 1:2 (amikacin:penicillin) and 1:100. Compositions outside of this preferred range also provide advantageous results, however, and are intended to be included within the scope of the present invention. As an example of a proposed human dose, a parenteral preparation may be used comprising 200 mg. amikacin sulfate and 400 mg. a penicillin of formula I. The dry-fill containing the amikacin and penicillin is dissolved in sterile water and then administered by injection as a single dose of the antibiotic combination. This proposed single dose might be administered about twice a day as a proposed daily human dosage. The particular dosage selected will, of course, be determined by the physician after considering the age, weight and condition of the subject and is determinable by those skilled in the art based on data presented herein and experience with other known penicillin-aminoglycoside combinations.

DESCRIPTION OF THE PREFERRED EMBODIMENT

EXAMPLE 1

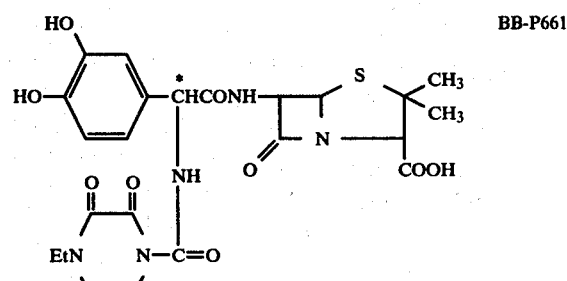

*Dextro

D-α-(4-Ethyl-2,3-dioxo-1-piperazinocarboxamido)-α-3,4-dihydroxyphenylacetic acid (2a)

To a cooled and stirred solution of 5.4 g (0.03 mole) of D(−)-3,4-dihydroxyphenylglycine in 60 ml of N sodium hydroxide was added dropwise at 0° to 5° C. a solution of 7.36 g (0.036 mole) of 4-ethyl-2,3-dioxo-1-piperazinylcarbonyl chloride in 70 ml of dry tetrahydrofuran (THF). The mixture was stirred at 5° to 10° C. for 30 minutes, during which it was maintained at pH 8-9 by addition of N sodium hydroxide. The reaction mixture was concentrated to 70 ml, acidified with conc. HCl and extracted with 400 ml of ethyl acetate-n-butanol (10:1). The extracts were dried over MgSO$_4$. After evaporation of the solvent, the residue (ca. 6 g) was chromatographed on silica gel (Wako-gel C-100, 150 g) by eluting with chloroform and then chloroform-methanol. The desired fractions were collected and evaporated to dryness to give 870 mg (8%) of the title compound, 2a. $[\alpha]_D^{22} = -84°$ (c=1, EtOH). M.p. 200°-205° C. (dec.).

ir: $\nu_{max}^{KBr}$ 1710, 1670, 1610, 1520, 1400, 1370, 1290, 1190 cm$^{-1}$.

uv: $\lambda_{max}^{Buffer(pH7)}$ 221 nm ($\epsilon$, 11500), 277 nm ($\epsilon$, 4700).

Anal. Calcd. for C$_{15}$H$_{17}$N$_3$O$_7$·H$_2$O: C, 48.78; H, 5.18; N, 11.28. Found: C, 48.68; H, 4.58; N, 10.87.

BB-P 661; Sodium 6-[D-α-(4-ethyl-2,3-dioxo-1-piperazinocarboxamido)-α-(3,4-dihydroxyphenyl)acetamido]penicillinate (3a)

To a cooled and stirred suspension of 351 mg (1 m mole) of 2a and 224 mg (2.2 m moles) of N-methylmorpholine in 10 ml of dry THF was added dropwise at −5° C. a solution of 130 mg (1.2 m moles) of ethyl chloroformate in 5 ml of dry THF and the mixture was stirred at −5° to −10° C. for one hour. To the mixture was added in one portion at −10° C. a solution of 432 mg (2 m moles) of 6-APA (6-aminopenicillanic acid) and 303 mg (3 m moles) of triethylamine in 10 ml of 50% aqueous THF and the mixture was stirred at −5° C. for 15 minutes and at room temperature for 30 minutes. The reaction mixture was concentrated to 5 ml, and the concentrate was acidified with 6 N HCl and extracted with 100 ml of ethyl acetate. The extracts were washed with a saturated NaCl solution, dried over MgSO$_4$ and concentrated to 30 ml. To the concentrate was added 1 ml of 1 M SEH (sodium 2-ethylhexanoate) in ethyl acetate and the resulting precipitate was collected by filtration, washed with ethyl acetate followed by ether and dried in vacuo over P$_2$O$_5$ to give 202 mg (35%) of BB-P 661, melting at 170°-180° C. (dec.).

ir: $\nu_{max}^{KBr}$ 1770, 1710, 1680, 1610, 1510, 1400, 1380, 1260, 1190 cm$^{-1}$.

uv: $\lambda_{max}^{Buffer(pH7)}$ 220 nm, sh ($\epsilon$, 14000), 265 nm, sh ($\epsilon$, 4600).

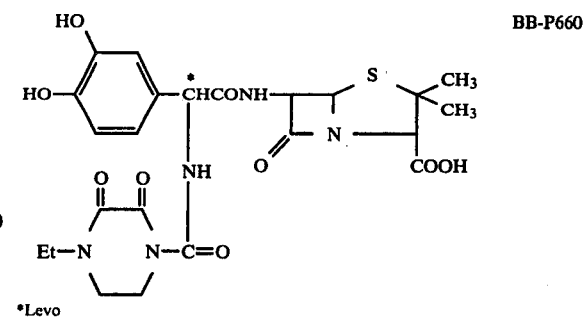

BB-P660

*Levo

L-α-(Ethyl-2,3-dioxo-1-piperazinocarboxamido)-α-3,4-dihydroxyphenylacetic acid (2b)

To a cooled and stirred solution of 2.66 g (0.02 mole) of L(+)-3,4-dihydroxyphenylglycine in 40 ml of N sodium hydroxide was added dropwise at 0°-5° C. a solution of b 4.5 g (0.022 mole) of 4-ethyl-2,3-dioxo-1-piperazinyl carbonyl chloride in 50 ml of dry THF. The mixture was stirred at 0°-5° C. for 30 minutes, during which it was maintained at pH 8-9 by addition of N sodium hydroxide. The reaction mixture was concentrated to 40 ml, acidified with conc. hydrochloric acid and extracted with 300 ml of ethyl acetate-n-butanol (10:1). The extract was dried over MgSO$_4$ and evaporated to dryness. The oily residue (ca. 4 g) was chromatographed on silica gel (C-200, 70 g) by eluting with chloroform and subsequently with chloroform-methanol. The desired fractions were collected and evaporated to dryness to give 1.52 g (21.5%) of the title compound (2b). m.p. 200°-205° C. (dec.), $[\alpha]_D^{22} = +79°$ (c=1, EtOH).

ir: $\nu_{max}^{KBr}$ 1710, 1670, 1610, 1520, 1400, 1370, 1290, 1190 cm$^{-1}$.

uv: $\lambda_{max}^{Buffer(pH7)}$ 221 nm ($\epsilon$, 10000), 277 nm ($\epsilon$, 4000)

Anal. Calcd. for C$_{15}$H$_{17}$N$_3$O$_7$·3/2H$_2$O: C, 47.62; H, 5.33; N, 11.11. Found: C, 47.45; H, 5.16; N, 9.21.

BB-P 660; Sodium 6-[L-α-(4-ethyl-2,3-dioxo-1-piperazinocarboxamido)-α-3,4-dihydroxyphenylacetamido]penicillanate (3b)

A solution of 130 mg (1.2 m moles) of ethyl chloroformate in 10 ml of dry THF was added dropwise at −5° C. to a cooled and stirred suspension of 351 mg (1 m mole) of 2b and 224 mg (2.2 m moles) of N-methylmorpholine in 10 ml of dry THF and the mixture was stirred at −5° to −10° C. for one hour. To the mixed anhydride solution was added in one portion at −10° C. a solution of 432 mg (2 m moles) of 6-APA and 303 mg (3 m moles) of triethylamine in 10 mg of 50% aqueous THF and the mixture was stirred at −5° C. for 10 minutes and at room temperature for 20 minutes. The reaction mixture was concentrated to 10 ml and the concentrate was washed with ether, acidified with dilute hydrochloric acid and extracted with 100 ml of ethyl acetate. The extract was washed with a saturated aqueous NaCl solution, dried over anhydrous MgSO$_4$ and concentrated to 30 ml. To the concentrate was added 0.9 ml (0.9 m mole) of SEH in ethyl acetate to afford a precipitate, which was collected by filtration, washed with ethyl acetate and ether and dried in vacuo over P$_2$O$_5$ to give 230 mg (50%) of BB-P660 melting at 170°-180° C. (dec.).

ir: $\nu_{max}^{KBr}$ 1770, 1720, 1680, 1610, 1510, 1400, 1375, 1260, 1190 cm$^{-1}$.

uv: $\lambda_{max}^{Buffer(pH7)}$ 220 nm ($\epsilon$, 13000), 265 nm ($\epsilon$, 3800).

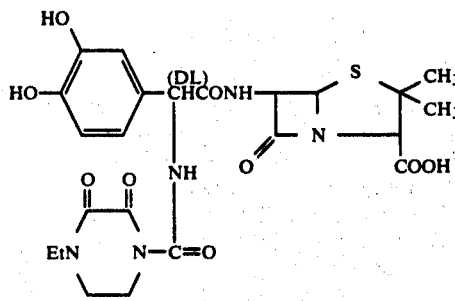

BB-P652

DL-$\alpha$-(4-ethyl-2,3-dioxo-1-piperazinocarboxamido)-$\alpha$-3,4-dihydroxyphenylacetic acid (2c)

To a cooled and stirred solution of 2.7 g (0.015 mole) of DL-$\alpha$-amino-$\alpha$-3,4-dihydroxyphenylacetic acid in 15 ml of N sodium hydroxide solution was added dropwise at 5°–10° C. a solution of 3.1 g (0.014 mole) of 4-ethyl-2,3-dioxopiperazine-1-carbonyl chloride in 5 ml of dry THF. The mixture was stirred for one hour at 10°–20° C., while the reaction mixture was maintained at pH 8–9 by adding portionwise 15 ml of N sodium hydroxide. The mixture was concentrated to 20 ml, acidified with concentrated hydrochloric acid and extracted with 400 ml of ethyl acetate-n-butanol (10:1). The extract was dried with MgSO$_4$ and evaporated to dryness. The residue was triturated with ether to give 1.8 g of the crude product, which was chromatographed on silica gel (C-200, 70 g) by eluting with chloroform and chloroformmethanol(20:1) successively. The desired eluate was collected and evaporated to dryness. The residue was triturated with ether to give 1.21 g (23%) of the pure product 2c, melting at 140° C. (dec.).

ir: $\nu_{max}^{KBr}$ 1710, 1680, 1520, 1400, 1370, 1290, 1190 cm$^{-1}$.

uv: $\lambda_{max}^{Buffer(pH7)}$ 225 nm ($\epsilon$, 11800), 277 nm ($\epsilon$, 4600)

nmr: $\delta_{ppm}^{DMSO-d6}$ 1.07 (3H, t, 7.5 Hz, CH$_2$C$\underline{H}_3$), 3.35 (2H, q, 2.5 Hz, C$\underline{H}_2$CH$_3$), 3.3–3.7 (2H, m, N—CH$_2$), 2.7–4.1 (2H, m, N—CH$_2$), 5.03 (1H, d, 7 Hz, CH—CO), 6.62 (2H, s, phenyl-H), 6.67 (1H, s, phenyl-H), 8.5–9.1 (2H, br, OH), 9.5 (1H, d, 7Hz, NH).

Anal. Calcd. for C$_{15}$H$_{17}$N$_3$O$_7$.½H$_2$O: C, 50.00; H, 5.03; N, 11.96. Found: C, 50.40; H, 4.87; N, 11.62.

BB-P 652: Sodium 6-[DL-$\alpha$-(4-ethyl-2,3-dioxo-1-piperazinocarboxamido)-$\alpha$-3,4-dihydroxyphenylacetamido]penicillanate (3c)

To a cooled and stirred suspension of 176 mg (0.5 m mole) of 2c and 112 mg (1.1 m moles) of N-methylmorpholine in 10 ml of dry THF was added at −10° C. a solution of 65 mg (0.6 m mole) of ethyl chloroformate in 5 ml of dry THF and the mixture was stirred at −5° to −10° C. for one hour. The reaction mixture became a clear solution. To the solution was added in one portion a solution of 216 mg (1 m mole) of 6-APA and 150 mg (1.5 m moles) of triethylamine in 10 ml of 50% aqueous THF. The mixture was stirred at −10° C. for 15 min. and at room temperature for 30 min. After concentration of the dried filtrate to 5 ml, the aqueous solution was acidified with dilute hydrochloric acid and extracted with 100 ml of ethyl acetate. The extract was washed with water and then with a saturated aqueous NaCl solution, dried with MgSO$_4$ and concentrated to 50 ml. To the concentrate was added 0.5 ml (0.5 m mole) of SEH in ethyl acetate. The resulting precipitate was collected by filtration, washed with ethyl acetate and ether and dried in vacuo over P$_2$O$_5$ to give 180 mg (63%) of BB-P 652, melting at 170°–180° C. (dec.).

ir: $\nu_{max}^{KBr}$ 1770, 1710, 1680, 1610, 1510, 1400, 1370, 1260, 1190 cm$^{-1}$.

uv: $\lambda_{max}^{Buffer(pH7)}$ 220 nm ($\epsilon$, 12000), 270 nm ($\epsilon$, 2600).

Biological activity

Minimum inhibitory concentrations (MIC) of BB-P 652, BB-P 660 and BB-P 661 were determined by serial two-fold agar dilution method using Steer's apparatus on Mueller-Hinton agar plates against S. aureus (6 strains), cephalothinsensitive gram-negative (Gn-I, 13 strains), cephalothinresistant gram-negative (Gn-II, 6 strains) and Ps. aeruginosa (64 strains). The results are shown in Tables 1 and 2 along with piperacillin and carbenicillin. Table 1 shows MIC values of representative strains selected from the test organisms used and Table 2 shows mean % relative activity of penicillins to carbenicillin which was calculated from geometric mean of MIC values in each group of the test organisms.

Against gram-positive bacteria, BB-P 652, BB-P 660 and BB-P 661 were almost as active as each other and less potent than piperacillin. The gram-negative activity of the dihydroxy penicillins depended on the configuration of the $\alpha$-carbon in the 6-acyl side chain. The D-isomer, (BB-P 661) was the most active of the three isomers and the L-isomer (BB-P 660) showed considerably decreased activity. BB-P 661 was about 8 times more active than piperacillin against cephalothin-sensitive gram-negative organisms and slightly less active against Pseudomonas and cephalothin-resistant strains.

Table 1.

| In vitro activity of anti-pseudomonal penicillins by agar dilution technique (Mueller-Hinton agar). | | | | | |
|---|---|---|---|---|---|
| | MIC (mcg/ml) | | | | |
| Organisms | BB-P 652 | BB-P 660 | BB-P 661 | Piperacillin | Carbenicillin |
| S. aureus Smith | 6.3 | 6.3 | 6.3 | 0.8 | 0.2 |
| S. aureus BX-1633 | 12.5 | 12.5 | 12.5 | 3.1 | 3.1 |
| E. coli Juhl | 0.8 | 6.3 | 0.4 | 1.6 | 3.1 |
| K. pneumoniae A9977 | 0.05 | 0.8 | 0.025 | 0.8 | 1.6 |
| P. mirabilis A9900 | 0.8 | 12.5 | 0.4 | 0.8 | 0.8 |
| P. vulgaris A9539 | 0.8 | >100.0 | 0.4 | 0.4 | 1.6 |
| E. cloacae A9656 | 1.6 | 12.5 | 1.6 | 1.6 | 1.6 |
| P. aeruginosa A15150 | 50.0 | >100.0 | 12.5 | 3.1 | 25.0 |
| P. aeruginosa A9843 | 3.1 | >100.0 | 0.8 | 6.3 | 100.0 |
| P. aeruginosa | 6.3 | >100.0 | 0.8 | 25.0 | >100.0 |

Table 2.

| Mean % relative activity of BB-P 652, BB-P 660 and BB-P 661 | | | | | | |
|---|---|---|---|---|---|---|
| | | Mean % relative activity* (carbenicillin = 100%) | | | | |
| Group of Organisms | No. of strains | BB-P 652 (DL) | BB-P 660 (L) | BB-P 661 (D) | Piperacillin | Carbenicillin |
| S. aureus | 6 | 25 | 22 | 22 | 56 | 100 |
| Gram-negative (Gn-I) | 13 | 1780 | 200 | 3030 | 360 | 100 |

Table 2.-continued

Mean % relative activity of BB-P 652, BB-P 660 and BB-P 661

| Group of Organisms | No. of strains | BB-P 652 (DL) | BB-P 660 (L) | BB-P 661 (D) | Pipera-cillin | Carbe-nicillin |
|---|---|---|---|---|---|---|
| Gram-negative (Gn-II) | 6 | 112 | 6 | 178 | 224 | 100 |
| Ps. aeruginosa | 64 | 271 | 26 | 418 | 637 | 100 |

*Mean % relative activity = $\frac{\text{Geometric mean MIC of carbenicillin}}{\text{Geometric mean MIC of test compound}} \times 100$

| Fraction No. | Peak | Weight (g.) |
|---|---|---|
| Fraction 1 | A, (B, minor) | 0.67 |
| Fraction 2 | B | 1.9 BB-P661 |
| Fraction 3 | C | 1.7 |
| Fraction 4 | D | 1.3 |
| Fraction 5 | E | 2.8 |

Among them Fraction 2 and Fraction 4 exhibited antipseudomonal activity. Fraction 2 was lyophilized to give 1.9 g. of desired product (BB-P661) melting at 205°–210° C. with gradual decomposition.

nmr: $\delta_{ppm}{}^{D_2O}$ 1.17 (3H, t, 7.5 Hz, N—CH$_2$CH$_3$), 1.43 (6H, s, 2-CH$_3$), 3.25–3.75 (4H, m, N—CH$_2$CH$_3$ and N—CH$_2$—), 3.75–4.10 (2H, m, N—CH$_2$—), 4.16 (1H, s, 3—H), 5.25–5.50 (3H, m, 5-H, 6-H and CHCO), 6.80–7.00 (3H, m, phenyl-H).

Table 3

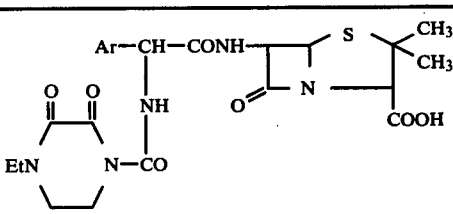

| Ar | Code No. | PD$_{50}$ (mice, im) | | | Blood Level (im, 20mg/kg) | |
|---|---|---|---|---|---|---|
| | | S. aureus Smith mg/kg | E. coli Juhl mg/kg | Ps. aerug. A9843 mg/kg | peak conc. mcg/ml | half life min |
| (D) | B-P 606[1] lot 1 lot 2 lot 3 | 0.8 | 3.3 45 | 35 25 40 | 4.9 6.2 9 | 44[2] 30[2] 29 |
| HO— HO— (DL) | BB-P 652 | 4.5 | 1.8 | 30 | 8.3 4.5 | 32 39 |
| HO— HO— (L) | BB-P 660 | 7.3 | 7.2 | >100 | 4 | 39 |
| HO— HO— (D) | BB-P 661 | 6.25 | 1.8 | 25 | 4 | 28 |

[1] piperacillin (Toyama's T-1220)
[2] route: sc

EXAMPLE 2

Preparation of BB-P661, 6-[D-α-(4-ethyl-2,3-dioxo-1-piperazinocarboxamido)-α-(3,4-dihydroxyphenyl)-acetamido]penicillanate by the mixed anhydride method is described above in Example 1. Recently HPLC analysis revealed that the product contained at least five components. The desired product was successfully isolated by preparative HPLC.

Purification of Crude BB-P661 by HPLC

As a crude sample of BB-P661 (19.8 g.) prepared by the mixed anhydride method illustrated by Example 1 showed five peaks, A, B, C, D and E, on the analytical HPLC chromatogram, it was fractionated into five portions by the preparative HPLC (Waters' System 500, cartridge μC$_{18}$, solvent: CH$_3$CN/H$_2$O = 10/90). The result is shown below:

EXAMPLE 3

The active ester method using N-hydroxysuccinimide (NOS) was applied to the preparation of BB-P661 to provide a better yield than that obtained by the mixed anhydride method.

Preparation By the Active Ester Method

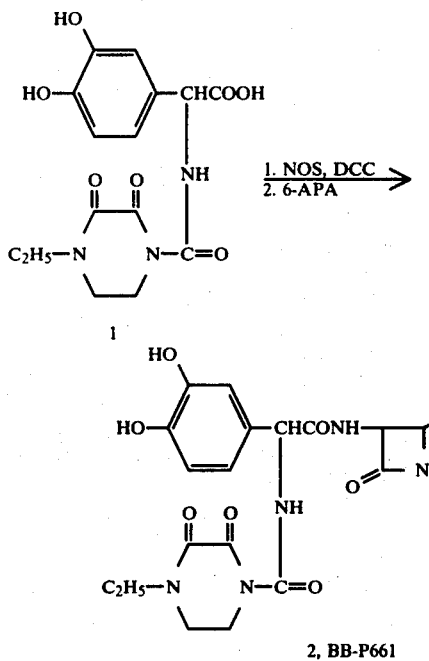

1, 2, BB-P661

A mixture of 42.1 g. (0.12 mole) of D-α-(4-ethyl-2,3-dioxo-1-piperazinocarboxamido)-α-(3,4-dihydroxyphenyl)-acetic acid (1), 16.56 g. (0.144 mole) of N-hydroxysuccinimide and 29.7 g. (0.144 mole) of dicyclohexylcarbodiimide (DCC) in 600 ml. of dry tetrahydrofuran (THF) was stirred at room temperature for 2 hours and the precipitated urea was removed by filtration. The filtrate was added in one portion to a cooled and stirred solution of 38.9 g. (0.18 mole) of 6-aminopenicillanic acid and 33 ml. (0.234 mole) of triethylamine in 400 ml. of water. The mixture was stirred at room temperature for 3 hours and concentrated to 400 ml. in order to remove most of the THF. The concentrate was treated with activated carbon and the filtrate was acidified with 40% phosphoric acid to pH 3 giving the product as an oily precipitate which was separated and triturated with water. The resulting solid was collected by filtration, washed with water and dried in vacuo over $P_2O_5$ to give 29.0 g. of the crude product (2). The mother liquid was extracted with ethyl acetate (2×500 ml.). The combined extracts were washed with water and saturated aqueous NaCl solution successively, dried over anhydrous $MgSO_4$ and evaporated to dryness. The residue was triturated with ether to give an additional amount (4.8 g.) of 2. A portion of the crude product (1.3 g.) was chromatographed on silica gel (Wako-gel C-200, 30 g.) eluting with chloroform and chloroform-methanol (10:1) successively. The desired fractions were collected and evaporated to dryness to give 420 mg. of 2 which showed a single peak on HPLC analysis.

We claim:

1. The acid of the formula

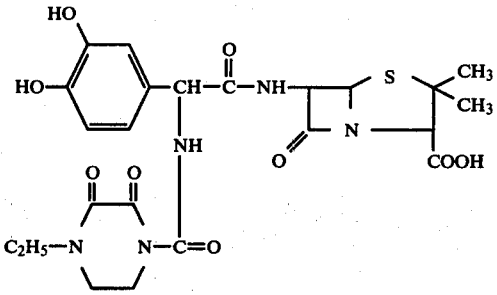

having the D-configuration in the 6-sidechain or a pharmaceutically acceptable acid thereof or an easily hydrolyzed ester thereof.

2. The acid of the formula

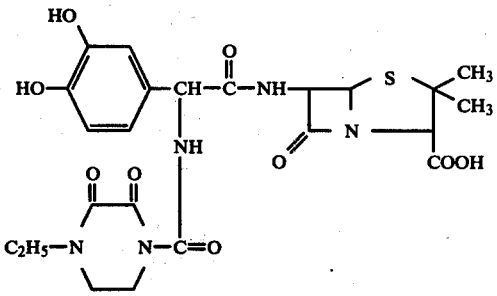

having the D-configuration in the 6-sidechain or a pharmaceutically acceptable salt thereof.

3. The sodium salt of the acid of claim 2.
4. The potassium salt of the acid of claim 2.
5. The pivaloyloxymethyl ester of the acid of claim 1.
6. The acetoxymethyl ester of the acid of claim 1.
7. The methoxymethyl ester of the acid of claim 1.
8. The 3-phthalidyl ester of the acid of claim 1.
9. The 5-indanyl ester of the acid of claim 1.

* * * * *

UNITED STATES PATENT AND TRADEMARK OFFICE
CERTIFICATE OF CORRECTION

PATENT NO. : 4,206,116
DATED : June 3, 1980
INVENTOR(S) : Takayuki Naito, Jun Okumura and Hideaki Hoshi It is certified that error appears in the above-identified patent and that said Letters Patent are hereby corrected as shown below:

In line 4 of Claim 1 delete "acid" and insert ---salt---.

Signed and Sealed this

Twelfth Day of August 1980

[SEAL]

Attest:

SIDNEY A. DIAMOND

Attesting Officer

Commissioner of Patents and Trademarks